Figure 1:
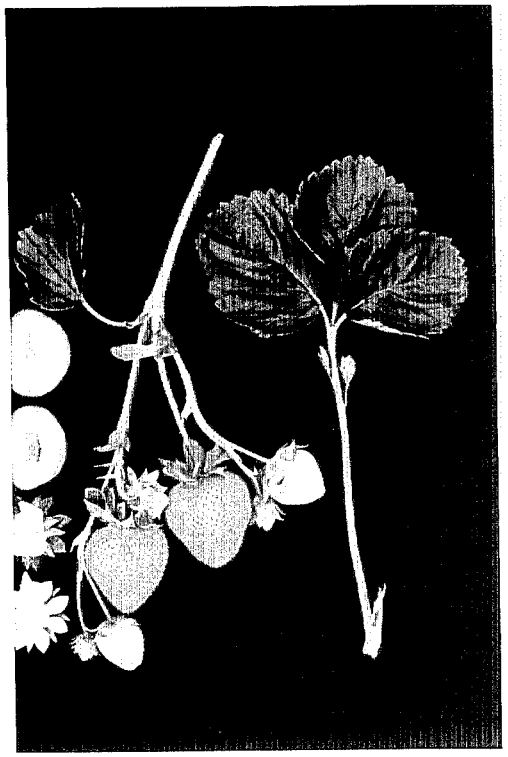

United States Patent [19]

Johnson, Jr. et al.

[11] Patent Number: Plant 6,231

[45] Date of Patent: Jul. 26, 1988

[54] STRAWBERRY PLANT 'KEN SHEEHY'

[75] Inventors: Harold A Johnson, Jr.; Amado Q. Amorao; Joseph I. Espejo, Jr., all of Watsonville, Calif.

[73] Assignee: Driscoll Strawberry Associates, Inc., Watsonville, Calif.

[21] Appl. No.: 862,338

[22] Filed: May 12, 1986

[51] Int. Cl.[4] ..... A01H 5/00

[52] U.S. Cl. ..... Plt./48

[58] Field of Search ..... Plt./48

*Primary Examiner*—James R. Feyrer

*Attorney, Agent, or Firm*—Townsend and Townsend

[57] ABSTRACT

A new and distinct spring bearing variety of strawberry plant, characterized by its firm good appearing fruit, both during the crown and subsequent crops. The variety has the ability to produce from April to October, but the transplants require correct chilling both at the nursery and cold storage if summer and fall crops are produced.

The variety is particularly distinguished by its late developing plant and crop during the spring. The fruit is distinguished because of its consistent appearance, flavor, and its good shelf life.

1 Drawing Sheet

This invention relates to a new and distinct variety of strawberry plant known as 'Ken Sheehy', which is a result of a cross of Driscoll Strawberry Associates, Inc. selection B6.117 and Driscoll Strawberry Associates, Inc. selection D.5.23.

The seedlings resulting from the aforementioned cross were grown and asexually multipled in Shasta County, Calif., and tested in the fruiting beds on the property of growers of the Driscoll Strawberry Associates, Inc. Clones of the seedlings were also held at the Propagation Nursery in Shasta County. One plant ws selected from the aforementioned group of seedlings and further asexually reproduced in the Shasta County Nursery of Driscoll Strawberry Associates, Inc. Test followed in various parts of California during intervening seasons on various properties of grower members of the Driscoll Strawberry Associates, Inc. These tests indicated the merits of 'Ken Sheehy' and resulted in its selection as a promising test variety.

In the drawing, FIG. 1 is a photograph of plant parts of the new variety, typical in size, shape, and color during June in the Watsonville area. The photograph was taken of plant parts taken from a plant that was transplanted from the nursery during November of the previous year. The berry in cross-section illustrates flesh color and characteristic core cavity. The inflorescence pictured illustrates typical branching and fruit size during this time of year. The picture shows two ripe berries, one a primary and one a secondary, and 5 green berries. These berries are mostly medium conic in outline, but may also be medium wedge or conic during the entire fruiting season. The picture shows pedicels of secondary of tertiary berries that are fused together. This condition may or may not be present on other inflorescences. The leaf pictured is typical showing bracts on the petiole. The serration on the leaflets are typical as are the limited amount of serrations on the sepals. The original photograph shows hair on pedicels holding tertiary fruit that are perpendicular to the pedicel. The flower present shows strong anthers that produce an abundance of pollen. The seed on the fruit is held in an exerted location in relation to the fruit surface which is also typical.

The novel plant becomes medium to large in size and is vigorous, but is only moderately vigorous early in its growth after being transplanted from the nursery. It is a spring variety, but has the ability of production throughout the season if the transplant doesn't receive excess chilling before being planted, or if chilling temperatures are not too great in total hours after being planted in fruiting beds. At the time of submitting this description the production was more consistent in Santa Maria than Watsonville. The crown crop and main crop are large and showy, but are considered late in ripening. Subsequent crops have fruit that is smaller, but consistent in size when comparing secondaries and tertiaries with primaries. Even though the mid and late summer production may be poor, the variety has the ability to crop during September and October.

This novel variety is distinguished from other varieties by its flowers, fruit, and plant characteristics. The plant foliage is darker than 'Heidi', U.S. Plant Pat. No. 3,1213. It also starts slower after being transplanted, but may actually become denser by mid-summer. 'Ken Sheehy' cannot be given the chilling 'Heidi' receives before being planted and still produce an adequate crop. The leaflets produce serrations that are not as acute at the apex as those produced by 'Heidi'. Even though the crown crop generally ripens later than 'Heidi', the fruit size is larger and more showy than 'Heidi'. The crops subsequent to the main spring crop are not as consistent in total amount or in uniform production through July to October as 'Heidi'. The total inflorescence length is usually equal, but the common peduncle is longer on 'Heidi'. The fruit appearance varies from 'Heidi' in that it is generally slightly darker than 'Heidi' when picked at the same maturity. It is equal to, or larger in size than, 'Heidi'. The fruit surface is generally smooth like 'Heidi', but doesn't show the white tips that 'Heidi' consistently produces even on well-shaped berries. There is a minimum of longitudinal ribbing on both varieties. Both varieties have a large showy calyx, but 'Ken Sheehy' products sepals with less serrations than 'Heidi'. 'Ken Sheehy' produces exerted seed in relationship with its fruit surface, even more exerted than 'Heidi'. The pedicels are thicker than 'Heidi', and they produce hair that is perpendicular to the pedicel, while the hair on 'Heidi' is irregularly parallel to the pedicel. The tertiary berries of 'Ken Sheehy' are larger than those of 'Heidi', and as a result 'Heidi' produces a higher percentage of fruit that will not make the standard necessary for acceptable market grade. The pedicels holding secondary and tertiary fruit are often fused together and this is not usually present on an inflorescence of 'Heidi'. Taste panels usually rate 'Heidi' and 'Ken Sheehy' equally good.

Both varieties are equal in holding tests, but 'Ken Sheehy' is rated firmer, but doesn't consistently hold its gloss as well as 'Heidi' after being held at room temperature.

The new variety appears to be equal to 'Heidi' in its susceptibility to twospotted mite, Verticillium wilt, and the Red Stele pathogen. As a seedling and selection, this new variety withstood the natural invasion of certain virus components found in central California without losing its ability to produce.

The varietal characteristics of the novel plant described below in detail were observed the first fruiting years after being transplanted during October and November during the previous year. The plants had been dug at a California high elevation nursery 3 to 5 weeks before the planting date. Observations were made mostly during July in Watsonville and Santa Maria, Calif., which are cool coastal areas near the Pacific Ocean. The color terminology is in accordance with the Munsell Color System.

*Plants.*—Medium to large, but low in vigor in early spring if given only enough chilling necessary to produce continuous production and a minimum amount of runners during the first year after being planted.

*Leaves.*—Medium to large in size. Central leaflet is usually 6 to 9 cm with the width mostly equal to the length. Petioles are long from July until the end of the season, mostly 16 to 25 , cm from basal bracts to petiolule. Petiolules are mostly 8 to 10 mm in length. Bracts are generally present on petioles. Leaflet serrations are medium deep and moderately acute at the apex. The color of the upper side of leaflets is 7.4 G&Y-2.3/4.0.

*Runners.*—Runners are vigorous, and abundant in fruiting beds if given excessive chilling. Moderate runner production at the nursery.

*Inflorescence.*—The inflorescence is 20 to 30 cm long, depending on the time of year, with the common peduncle mostly 10 to 15 cm in length. Pedicels are considered thick and strong. Pedicels holding the primary berry originate mostly at the axil formed by secondary peduncles. Primary and secondary fruit often ripen at the same time, and are often equal in size. Hair on pedicels 20 mm below tertiary flowers and are perpendicular to the pedicel. Pedicels of secondary and tertiary berries are often fused together. Flowers are large and showy producing anthers with an abundance of pollen. Flowers may be visible above the plant in the spring, but not as visible during subsequent crops in the summer and fall.

*Fruit.*—Crown crop berries are late in maturing, but large in size and with good appearance. Main crop primaries are larger, but July crop primaries are mostly 40 mm in length and width. Secondary berries are often as large as primaries, and tertiary berries are often as large as primaries, and tertiary berries are usually large enough to make grade for marketing. Berries are round shouldered, not necked, and are conic to medium wedge in outline as described in the USDA Bulletin No. 1043. Fruit surface is mostly smooth, not ribbed, and all seed is fertilized with folded seedy tips usually not present. The fruit surface gloss is considered good, and the flesh and skin firm. Seed are held exerted in relationship to the fruit surface, not sunken. Fruit produced during October develops seed that is more exerted than at other times of year. Seed is minimum in size, and is yellow, but is prone to darken especially during the crown crop. The berry has a high dessert quality. The fruit surface color is 6.8R-2.6/9.4, and the flesh color near the surface is 4.3Y-6.6/11.8.

*Calyx.*—Large in diameter with those on primary berries 40 to 45 mm in diameter. Sepals are large and abundant. Sepals are mostly elliptical in outline, and serrations are not abundant. The calyx is usually held free of the fruit surface, not reflexed or clasping. Color of sepals on side facing fruit is 8.2GY-3.2/6.1.

We claim:

1. The new and distinct variety of strawberry plant herein described and illustrated, and identified by the characteristics enumerated above.

* * * * *